(12) United States Patent
Creaven et al.

(10) Patent No.: US 8,231,048 B2
(45) Date of Patent: Jul. 31, 2012

(54) TEST-SENSOR CARTRIDGE

(75) Inventors: John P. Creaven, Granger, IN (US);
Dijia Huang, Granger, IN (US);
Weiping Zhong, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 470 days.

(21) Appl. No.: 12/515,363

(22) PCT Filed: Nov. 6, 2007

(86) PCT No.: PCT/US2007/023367
§ 371 (c)(1),
(2), (4) Date: May 18, 2009

(87) PCT Pub. No.: WO2008/063405
PCT Pub. Date: May 29, 2008

(65) Prior Publication Data
US 2010/0072270 A1 Mar. 25, 2010

Related U.S. Application Data

(60) Provisional application No. 60/860,187, filed on Nov. 20, 2006.

(51) Int. Cl.
*G06F 17/00* (2006.01)
(52) U.S. Cl. .................................................... 235/375
(58) Field of Classification Search .................. 235/375, 235/462.01; 600/319, 365, 561, 584
See application file for complete search history.

(56) References Cited

U.S. PATENT DOCUMENTS

| | | | |
|---|---|---|---|
| 5,588,555 A | 12/1996 | Kanamori | |
| 5,599,505 A | 2/1997 | Fujisaki | |
| 7,654,411 B2 * | 2/2010 | Boots et al. | 220/835 |
| 2003/0191415 A1 | 10/2003 | Moerman | |
| 2006/0035300 A1 * | 2/2006 | Yamaoka et al. | 435/14 |
| 2008/0131919 A1 * | 6/2008 | Yamaoka et al. | 435/14 |
| 2009/0112076 A1 * | 4/2009 | Estes et al. | 600/365 |
| 2010/0235439 A1 * | 9/2010 | Goodnow | 709/203 |

FOREIGN PATENT DOCUMENTS

| | | |
|---|---|---|
| EP | 1359419 | 11/2003 |
| EP | 1607137 | 12/2005 |

OTHER PUBLICATIONS

Written Opinion corresponding to International Patent Application No. PCT/US2007/023367, European Patent Office, dated Mar. 31, 2008, 6 pages.
International Search Report corresponding to International Patent Application No. PCT/US2007/023367, European Patent Office, dated Mar. 31, 2008, 4 pages.

* cited by examiner

*Primary Examiner* — Tuyen K Vo
(74) *Attorney, Agent, or Firm* — Nixon Peabody LLP

(57) ABSTRACT

A test-sensor cartridge including a plurality of test sensors adapted to assist in determining an analyte concentration of a fluid sample. The cartridge further includes a plurality of walls forming a cavity therein. The cavity is adapted to include the plurality of test sensors. At least one of the plurality of walls forms at least one aperture. The cartridge further includes a lid adapted to enclose the cavity. The cartridge further includes a locking feature adapted to lock the lid to one or more of the walls. The locking feature is adapted to be disengaged by the at least one aperture receiving a projection of an analyte-testing instrument.

14 Claims, 8 Drawing Sheets

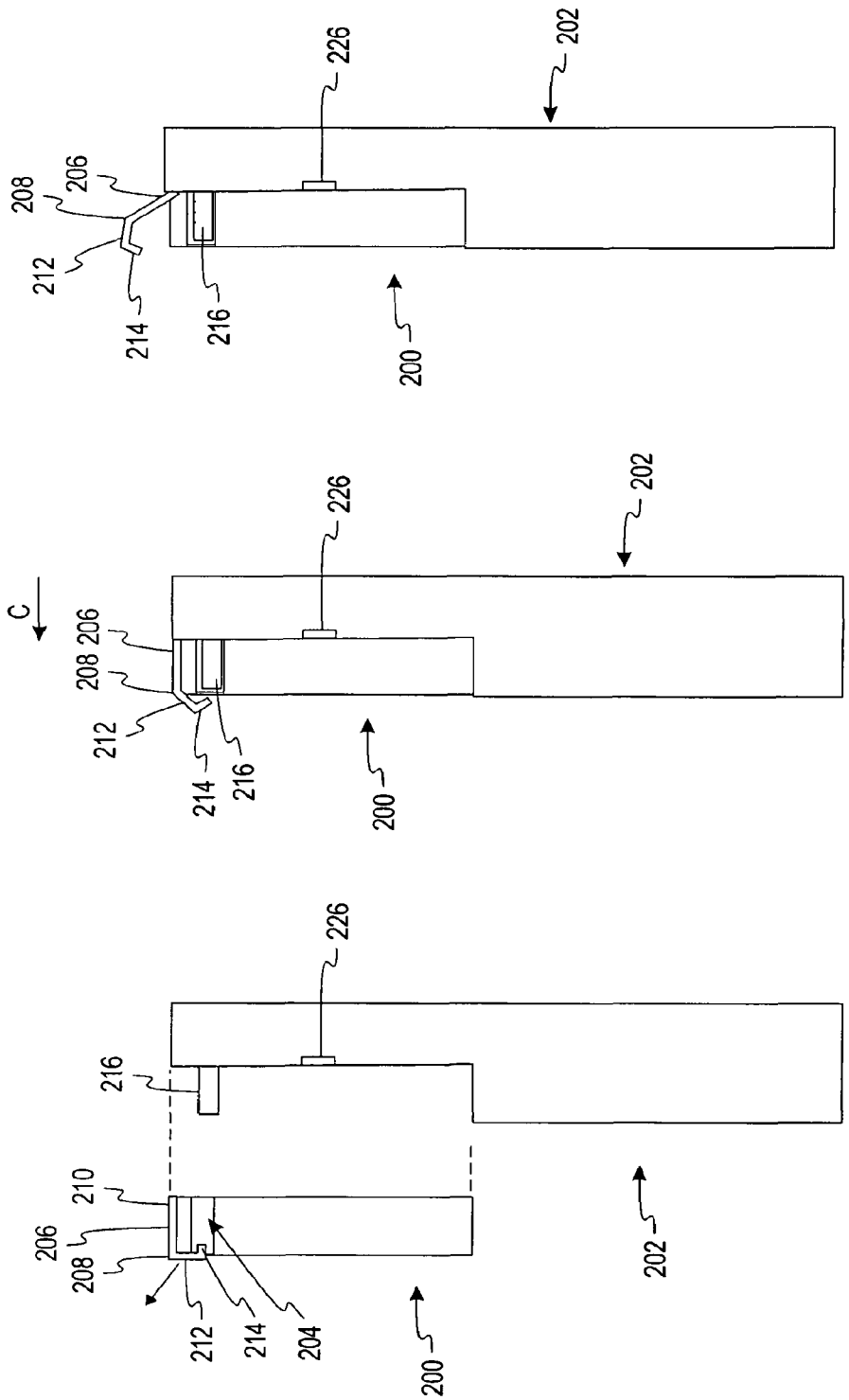

TEST-SENSOR CARTRIDGE

CROSS-REFERENCE TO RELATED APPLICATIONS

This application is a U.S. national phase of International Application No. PCT/US2007/023367, filed Nov. 6, 2007, which claims the benefit of priority of U.S. Provisional Application No. 60/860,187, filed on Nov. 20, 2006, both of which are incorporated by reference in their entireties.

FIELD OF THE INVENTION

The present invention relates generally to sensor-dispensing instruments and, more particularly, to test-sensor cartridges for assisting in ensuring compatibility with analyte-testing instruments (e.g., meters).

BACKGROUND OF THE INVENTION

The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets. The results of such tests may be used to determine what, if any, insulin and/or other medication needs to be administered. In one type of testing system, test sensors are used to test a fluid such as a sample of blood.

One method of monitoring an individual's blood glucose level is with a portable, hand-held blood glucose testing device (e.g., a meter). To determine the blood glucose level with the meter, a lancet device may be used with a needle lancet that pierces the skin tissue and allows a whole blood sample to form on the skin's surface. Once the requisite amount of blood forms on the skin's surface, the blood sample is transferred to a test sensor. The test sensor is generally placed in an opening in the body of the meter.

Test-sensor cartridges are commonly used to individually dispense test sensors to be used for testing an analyte in a fluid. The cartridges are used to store multiple sensors and allow users to carry multiple sensors around within a single enclosure. During testing, a blood or body fluid sample may be placed on the sensor and analyzed with the meter or instrument to determine the concentration of the analyte being examined.

The test-sensor cartridges may be incorporated directly into, for example, glucose meters to dispense test sensors for use with the meter. The cartridges may include features designed to mate with corresponding features inside of a meter to assist in indexing and/or excising the test sensors located within the cartridges. Alternatively, the cartridges may be kept separate from the meter. In such embodiments, a user may remove a single sensor from the cartridge to perform an analyte test. The cartridges assist in preventing or inhibiting test sensors from being exposed to the environment until they are required for use. Exposure to the environment (e.g., humidity, contaminants, or the like) may damage the test sensors, thereby altering test results.

Because different types of test sensors or test-sensor versions may have significant differences associated therewith, a problem occurs when a test sensor is used with a meter that was not designed to be used with the test sensor. This may occur, for example, when a user tests with a test sensor being placed into a meter that is not compatible with the test sensor. Alternatively, problems may occur if a meter is unable to distinguish the type and/or generation of test sensor being used or the calibration information associated therewith. Different types of test sensors may include different types of sensor reagent, which may influence items such as, for example, the amount of fluid sample needed and the length of time required for the reagent to react with the analyte to determine the analyte concentration. Furthermore, different test sensors may correspond with different assay parameters, protocols, and/or programs including test sequences, test times, algorithms, voltage, calibration information, expiration dates, or the like.

Many existing meters require that a user perform some affirmative act to notify the meter that a new test-sensor cartridge is being used so that the meter may calibrate and/or modify its testing parameters, protocols, and/or programs accordingly. For example, the user may be required to remove a code chip corresponding with the previously used cartridge and replace it with a code chip corresponding with a new cartridge. Oftentimes, however, the user minimizes the importance of performing such a notification step and/or forgets to change the code chip. Users may view this step as being optional and, in the interest of time, choose to skip the step altogether. Furthermore, because testing may be performed without notifying the meter of the type of cartridge and/or test sensors being used, it is relatively easy for a user to overlook performing this step.

Because meters are generally designed to perform protocols and run programs associated with certain test sensors, mismatching test-sensor cartridges and meters generally yields inaccurate test results. Inaccurate test results may result in dangerous analyte levels (e.g., hyperglycemic or hypoglycemic conditions) being undetected, which may be dangerous for a user and may have serious health-related consequences. At a minimum, mismatching test-sensor cartridges and meters may require extra testing, which may be inconvenient and expensive for a user.

It would be desirable to provide analyte-testing instruments (e.g., test-sensor cartridges) that inhibit or prevent using a meter with unsuitable types and/or generations of test-sensor cartridges.

SUMMARY OF THE INVENTION

According to one embodiment of the present invention, a test-sensor cartridge comprises a plurality of test sensors adapted to assist in determining an analyte concentration of a fluid sample. The cartridge further comprises a plurality of walls forming a cavity therein. The cavity is adapted to include the plurality of test sensors. At least one of the plurality of walls forms at least one aperture. The cartridge further comprises a lid adapted to enclose the cavity. The cartridge further comprises a locking feature adapted to lock the lid to one or more of the walls. The locking feature is adapted to be disengaged by the at least one aperture receiving a projection of an analyte-testing instrument.

According to another embodiment of the present invention, a test-sensor cartridge comprises a plurality of test sensors adapted to assist in determining an analyte concentration of a fluid sample. The cartridge further comprises a plurality of walls forming a cavity therein. The cavity is adapted to include the plurality of test sensors. At least one of the walls forms at least one aperture. The cartridge further comprises a lid adapted to enclose the cavity. The cartridge further comprises a coding feature positioned on at least one of the walls or the lid. The cartridge further comprises a locking feature adapted to lock the lid to one or more of the walls. At least a portion of the locking feature is positioned within the at least one aperture. The locking feature is adapted to be disengaged by the at least one aperture receiving a projection of an analyte-testing instrument. The coding feature is adapted to be read by a reading device positioned on the analyte-testing instrument.

According to one process of the present invention, a method of modifying testing parameters of an analyte-testing instrument comprises the act of providing a test-sensor cartridge including a plurality of walls forming a cavity therein. The cavity is adapted to include a plurality of test sensors. At least one of the walls forms at least one aperture. The cavity is enclosed by a lid having a locking feature adapted to lock the lid to one or more of the walls. The test sensors are adapted to assist in the determination of a concentration of an analyte in a fluid sample. At least one of the lid or the walls has a coding feature being positioned thereon. The method further comprises the act of providing an analyte-testing instrument having at least one projection located thereon. The analyte-testing instrument includes a reading device. The method further comprises the act of disengaging the locking feature by contacting the cartridge to the analyte-testing instrument such that the at least one projection mates with the at least one aperture. The method further comprises the act of reading the coding feature using the reading device. The method further comprises the act of modifying at least one testing parameter of the analyte-testing instrument based on information received by reading the coding feature.

The above summary of the present invention is not intended to represent each embodiment or every aspect of the present invention. Additional features and benefits of the present invention are apparent from the detailed description and figures set forth below.

BRIEF DESCRIPTION OF THE DRAWINGS

FIG. 4a is a cross-sectional side view of a test-sensor cartridge and an analyte-testing instrument according to one embodiment of the present invention where the cartridge is in a locked position.

FIG. 4b is a cross-sectional side view of the cartridge and analyte-testing instrument of FIG. 4a where the cartridge is in an intermediate position.

FIG. 4c is a cross-sectional side view of the cartridge and analyte-testing instrument of FIGS. 4a,b where the cartridge is in an open position.

DESCRIPTION OF ILLUSTRATED EMBODIMENTS

The present invention is directed to forcing communication between a meter and a test-sensor cartridge so that the meter may receive calibration information from the cartridge. The present invention is further directed to inhibiting or preventing using a meter or meter parameters, protocols, or programs with an unsuitable type and/or generation of test-sensor cartridge. The test sensors (e.g., biosensors) dispensed from the cartridge may be used to assist in determining an analyte concentration in a fluid sample. Some examples of the types of analytes that may be collected and analyzed include glucose, lipid profiles (e.g., cholesterol, triglycerides, LDL, and HDL), microalbumin, hemoglobin, $A_1C$, fructose, lactate, or bilirubin. The present invention is not limited, however, to these specific analytes, and it is contemplated that other analyte concentrations may be determined. The analytes may be in, for example, a whole blood sample, a blood serum sample, a blood plasma sample, or other body fluids like ISF (interstitial fluid) and/or urine. One non-limiting example of a use of the test-sensor cartridge and meter is to determine the glucose concentration in a user's blood, plasma, or ISF.

Test sensors used in determining analyte concentrations in one embodiment include a capillary channel that extends from the front or testing end of the test sensor to biosensing or reagent material disposed in the test sensor. The reagent generally includes an appropriately selected enzyme to react with the desired analyte or analytes to be tested. The reagent may be stored within the test sensor in a dried form to promote an extended shelf life of the test sensor. When the testing end of the test sensor is placed into fluid (e.g., blood that is accumulated on a person's finger after the finger has been pricked), a portion of the fluid is drawn into the capillary channel by capillary action. The fluid then mixes with the reagent material in the test sensor and chemically reacts with the reagent material so that an electrical signal indicative of the analyte (e.g., glucose) level in the fluid being tested is supplied and subsequently transmitted to a meter.

Figure 1:
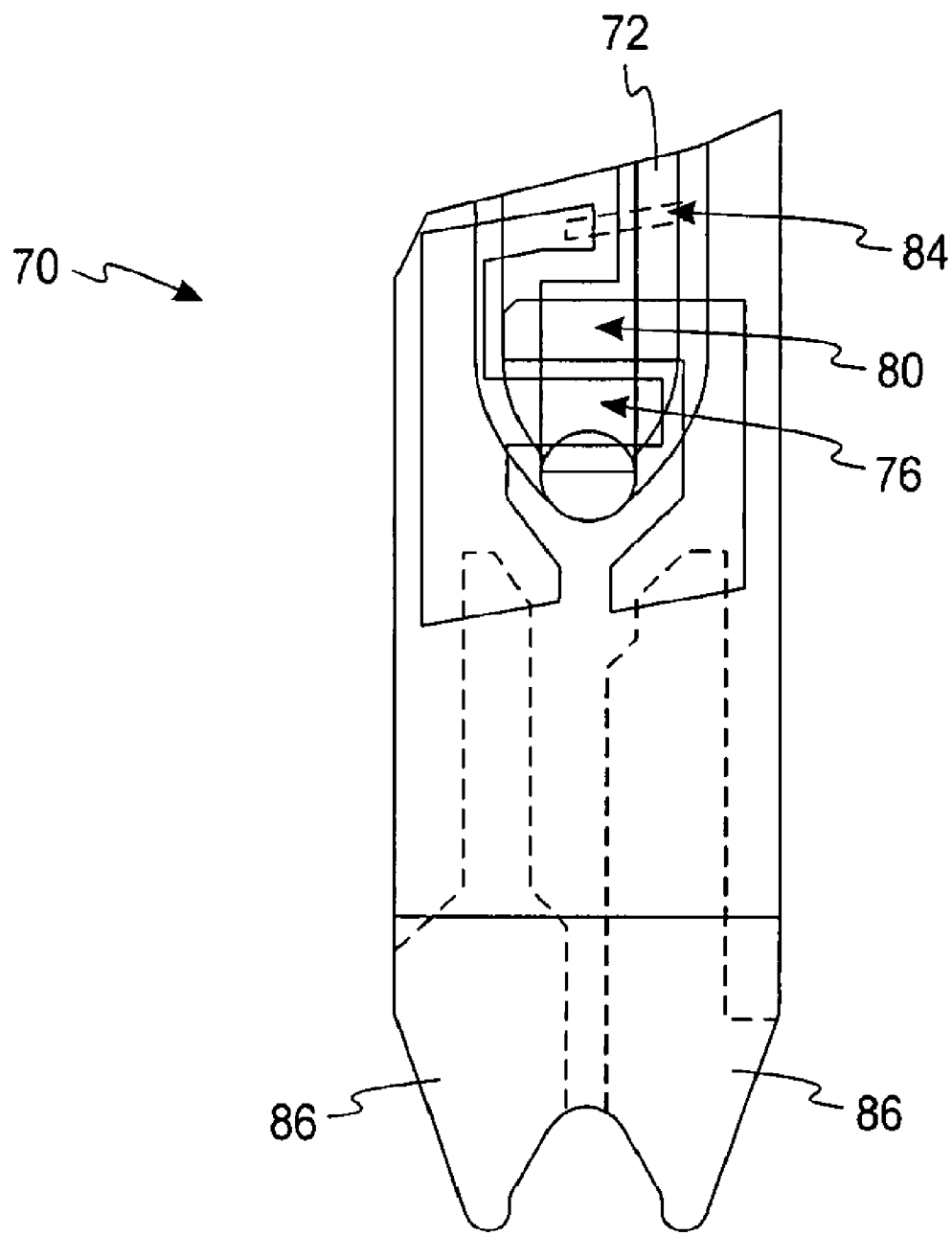
FIG. 1 is a top view of a test sensor according to one embodiment.

One type of test sensor that may be used is an electrochemical test sensor. One non-limiting example of an electrochemical test sensor is shown in FIG. 1. FIG. 1 depicts a test sensor 70 that includes a capillary channel 72, an area for meter contacts 86, and a plurality of electrodes 76, 80, 84. The capillary channel 72 contains reagent. The plurality of electrodes includes a counter electrode 76, a working (measuring) electrode 80, and an optional trigger electrode 84. The trigger electrode 84 may assist in determining whether a sufficient blood sample has been placed on the sensor 70. The electrochemical test sensor may also contain other numbers and/or types of electrodes. Examples of electrochemical test sensors, including their operation, may be found in, for example, U.S. Pat. No. 6,531,040 assigned to Bayer Corporation. It is contemplated that other electrochemical test sensors may be employed. It is also contemplated that other types of test sensors may be used including, but not limited to, optical test sensors.

Figure 2:
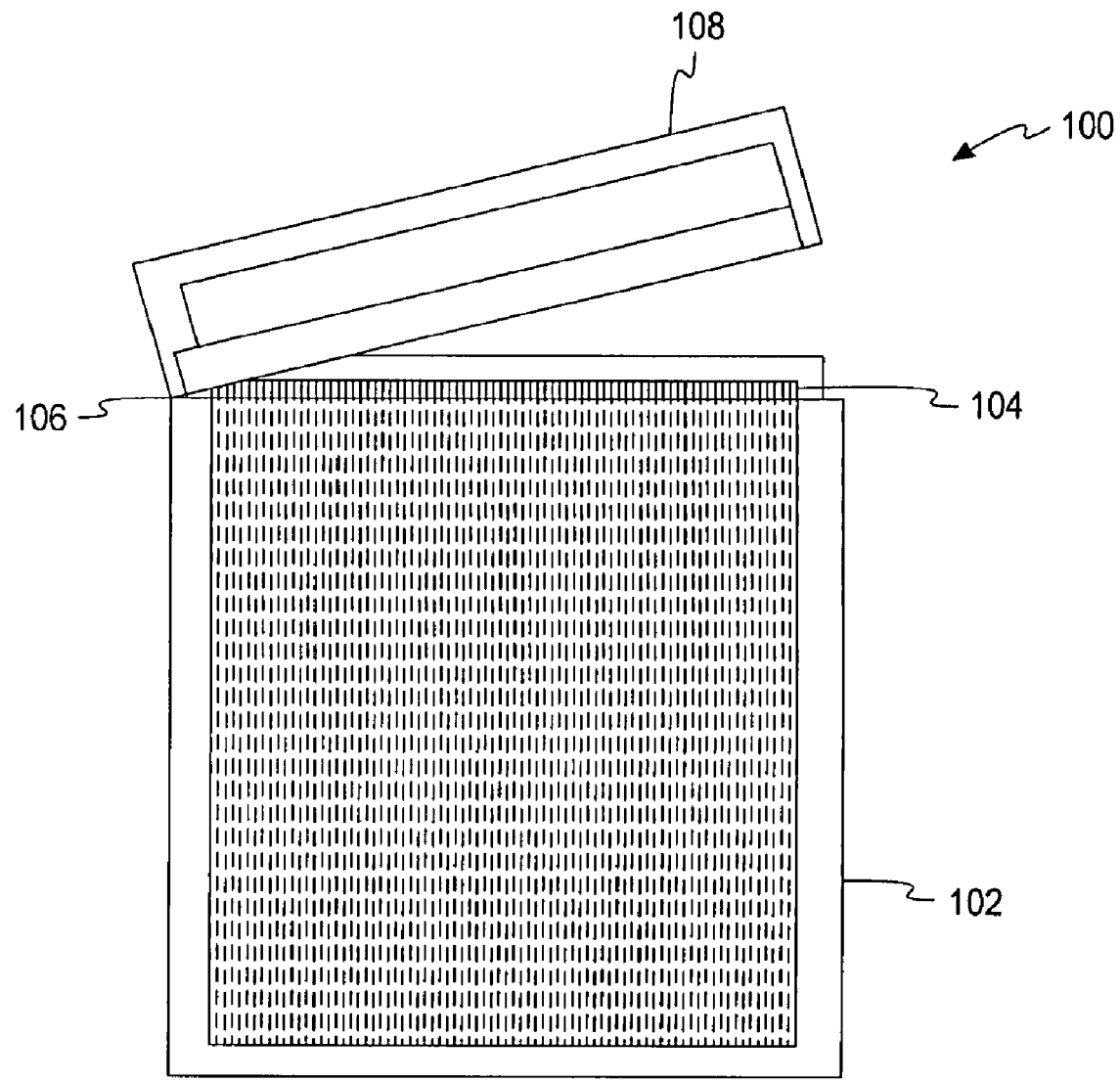
FIG. 2 is a cross-sectional side view of a test-sensor cartridge according to one embodiment.

A plurality of test sensors may be stored in a disposable test-sensor cartridge. The test-sensor cartridge may include any type of container adapted to contain test-sensors including, but not limited to bottles, disks, or the like. For example, the plurality of test sensors may be stored in a cartridge where the test sensors are generally radially aligned and individually packaged in sensor cavities (e.g., a blister-type pack). Another example of a disposable cartridge 100 is depicted in FIG. 2. The disposable cartridge 100 of FIG. 2 comprises a housing 102, a plurality of stacked test sensors 104, a hinge mechanism 106, and a lid 108. The cartridge 100 is adapted to be disposed of after each of the plurality of test sensors 104 has been removed and used. It is also contemplated that the cartridge 100 may be refilled and, thus, reused. The desiccant compartment of reusable cartridges generally should be replaced when a reusable cartridge is refilled.

The test-sensor cartridges of the embodiments of the present invention are generally unable to be opened until the cartridges contact an unlocking feature on a meter. The unlocking feature may be a projection that fits within a corresponding aperture of the cartridge. Requiring contact between the cartridge and the meter assists in inhibiting or preventing the cartridge from being used with an unsuitable meter and/or applying unsuitable testing parameters, protocols, or programs during analyte testing.

Figure 3A:
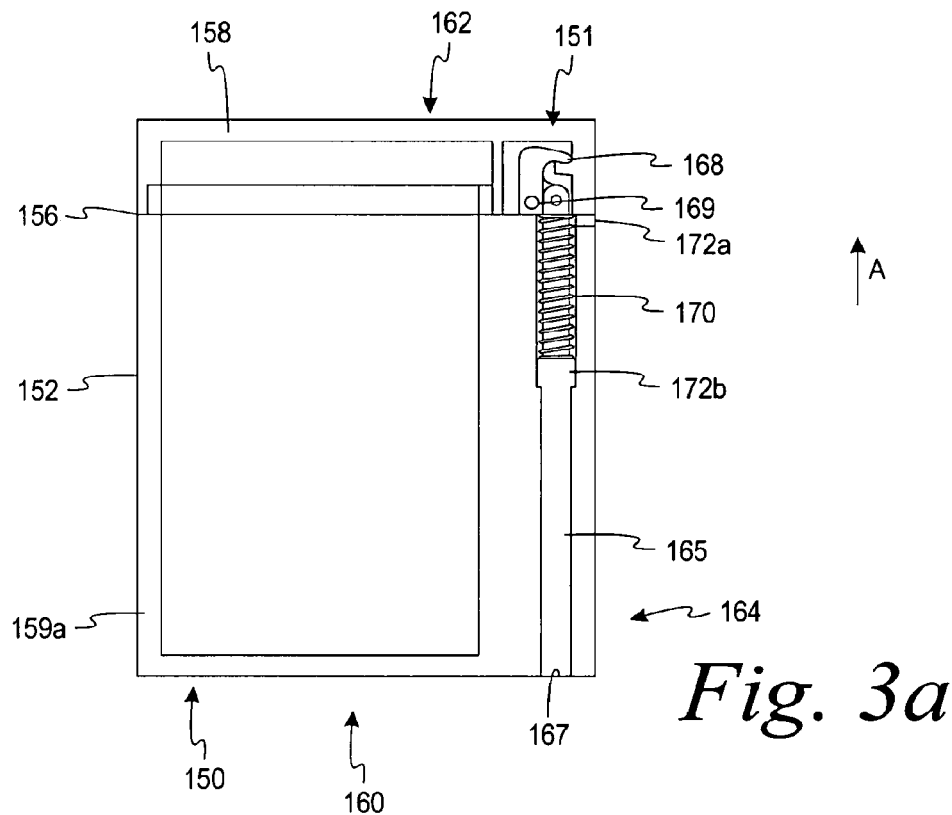
FIG. 3a is a cross-sectional side view of a test-sensor cartridge in a closed position according to an embodiment of the present invention.

In the embodiment of FIGS. 3a,b, for example, a test-sensor cartridge 150 having a release lock feature 151 is shown. Like the cartridge 100 of FIG. 2, the cartridge 150 comprises a housing 152, a hinge mechanism 156, and a lid 158. The housing 152 includes a plurality of walls including a front wall 159a, a back wall (not shown) opposite the front wall 159a, a first side wall 159b (see FIG. 3c), a second side wall (not shown) opposite the first side wall 159b, and a bottom 160. The walls (e.g., walls 159a,b) form a cavity 161 adapted to hold a plurality of stacked test sensors (not shown) therein. The lid 158 is positioned at a top end 162 of the cartridge 150 and is adapted to enclose the cavity 161. The lid 158 includes a notch 163 positioned at a top 162 of a first end 164 of the cartridge 150. The release lock feature 151 is positioned at the first end 164 of the cartridge 150 and includes a rod 165 housed within the cartridge 150 in a generally vertical position. The rod 165 is positioned within an aperture 166 formed at the first end 164 of the cartridge 150. The aperture 166 extends through the bottom 160 of the cartridge 150. In the illustrated embodiment, a bottom 167 of the rod 165 is generally flush with the bottom 160 of the cartridge 150. It is contemplated, however, that the rod 165 may be shortened (i.e., recessed), in the cartridge 150. The rod 165 is coupled to a latch 168 at the top end 162 of the cartridge 150. The latch 168 is rotatable about a pivot point 169. The release lock feature 151 further includes a spring 170 positioned between a first spring retainer 172a and a second spring retainer 172b.

FIG. 3a shows the cartridge 150 with the lid 158 in a closed position. In the closed position, the latch 168 generally wraps around the notch 163 located in the interior of the lid 158 at the top 162 of the first end 164 of the cartridge 150, thereby locking the lid 158 to at least one of the walls (e.g., front wall 159a, first side wall 159b) into a closed position relative to the cartridge 150. Thus, a user would be unable to open the lid 158 to remove a test sensor (not shown) within the cartridge 150.

Figure 3B:
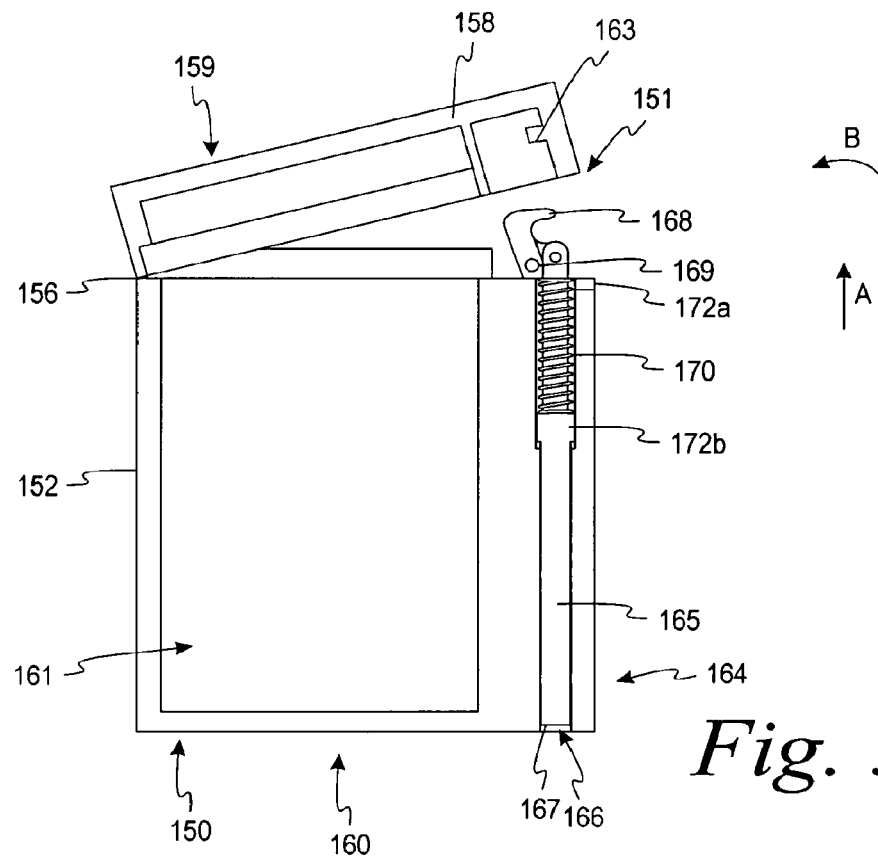
FIG. 3b is a cross-sectional side view of the cartridge of FIG. 3a in an open position.
Figure 3C:
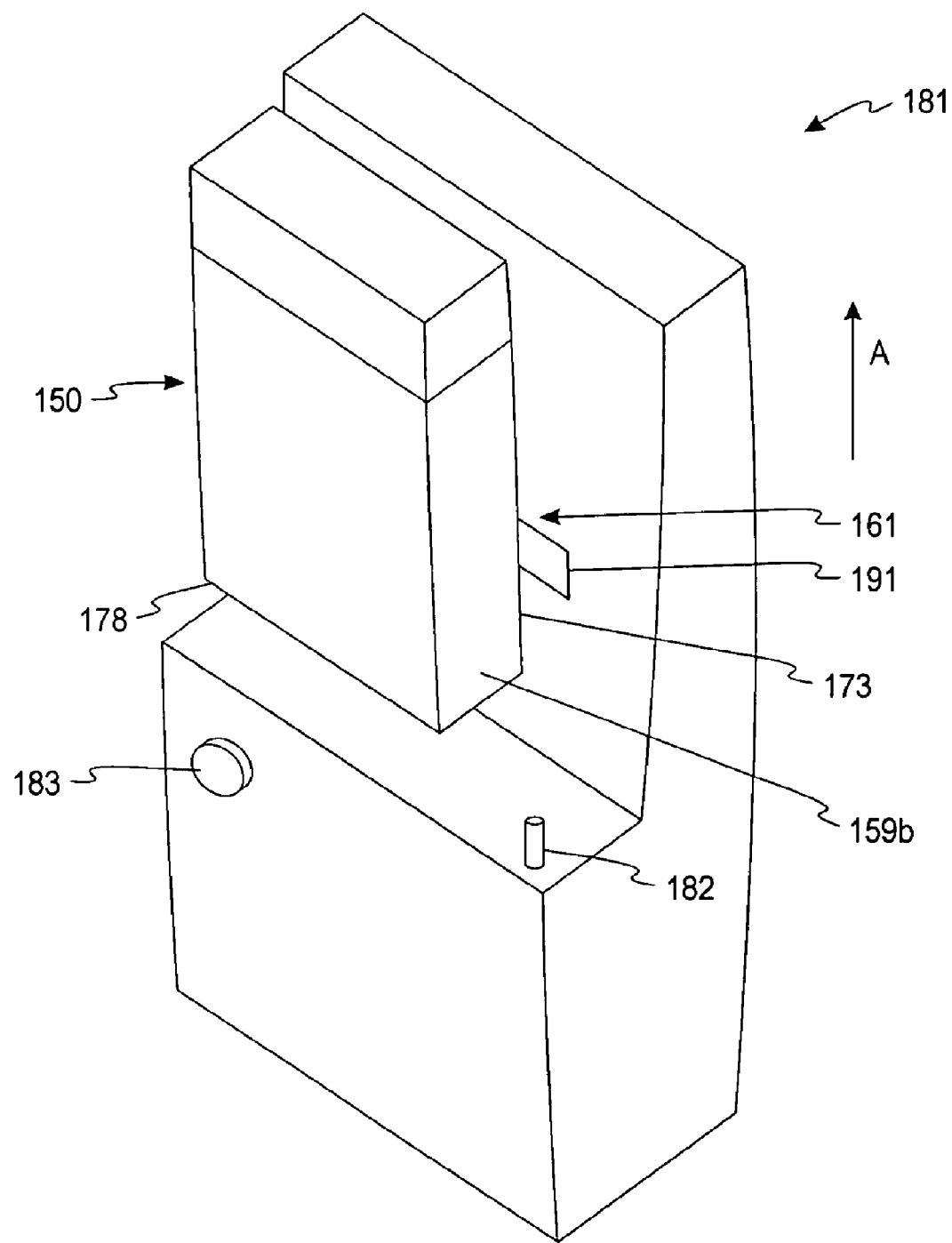
FIG. 3c is a perspective view of the cartridge of FIGS. 3a,b making contact with an analyte-testing instrument.

Referring now to FIG. 3c, to open the cartridge 150, the aperture 166 formed at the bottom 160 of the cartridge 150 is required to contact a meter 181 such that the bottom 167 of the rod 165 contacts a corresponding projection 182 suitably positioned on the meter 181. The projection 182 pushes the bottom 167 of the rod 165 upward in the direction of Arrow A. The upward movement of the rod 165 causes the spring 170 to compress between the first and second spring retainers 172a,b, thereby causing the latch 168 to rotate about the pivot point 169 in the direction of Arrow B (FIG. 3b). The rotation of the latch 168 releases the latch 168 from being obstructed by the notch 163. The rotation of the latch 168 allows the lid 158 to be lifted off of the cartridge 150, which allows the cartridge 150 to be opened. Thus, a user may remove a test sensor from the opened cartridge 150 (see FIG. 3b).

In one embodiment, after the user removes the cartridge 150 from the projection 182 of the meter, the spring 170 forces the release lock feature 151 to return to the locked position of FIG. 3a. Thus, when the user closes the lid 158, the latch 168 again becomes obstructed by the notch 163, thereby relocking the cartridge 150.

In another embodiment, the release lock feature 151 is only required to be unlocked once. Thereafter, the lid 158 of the cartridge 150 may be closed without locking. This may be desirable since the cartridge 150 need only contact the meter a single time for the meter to recognize the type of cartridge, and thus, the type of test sensor, being used. Once the meter recognizes the type of cartridge being used, the meter calibrates and/or modifies its testing parameters, programs, and/or protocols accordingly.

In yet another embodiment, the cartridge 150 may remain coupled to the meter 181 using any suitable means. When the cartridge 150 is empty and is to be replaced with a new (e.g., full) cartridge, the user may, for example, press a release button 183 on the meter 181 to remove the cartridge 150 from the meter 181 so that another cartridge 150 may be introduced.

Figure 3D:
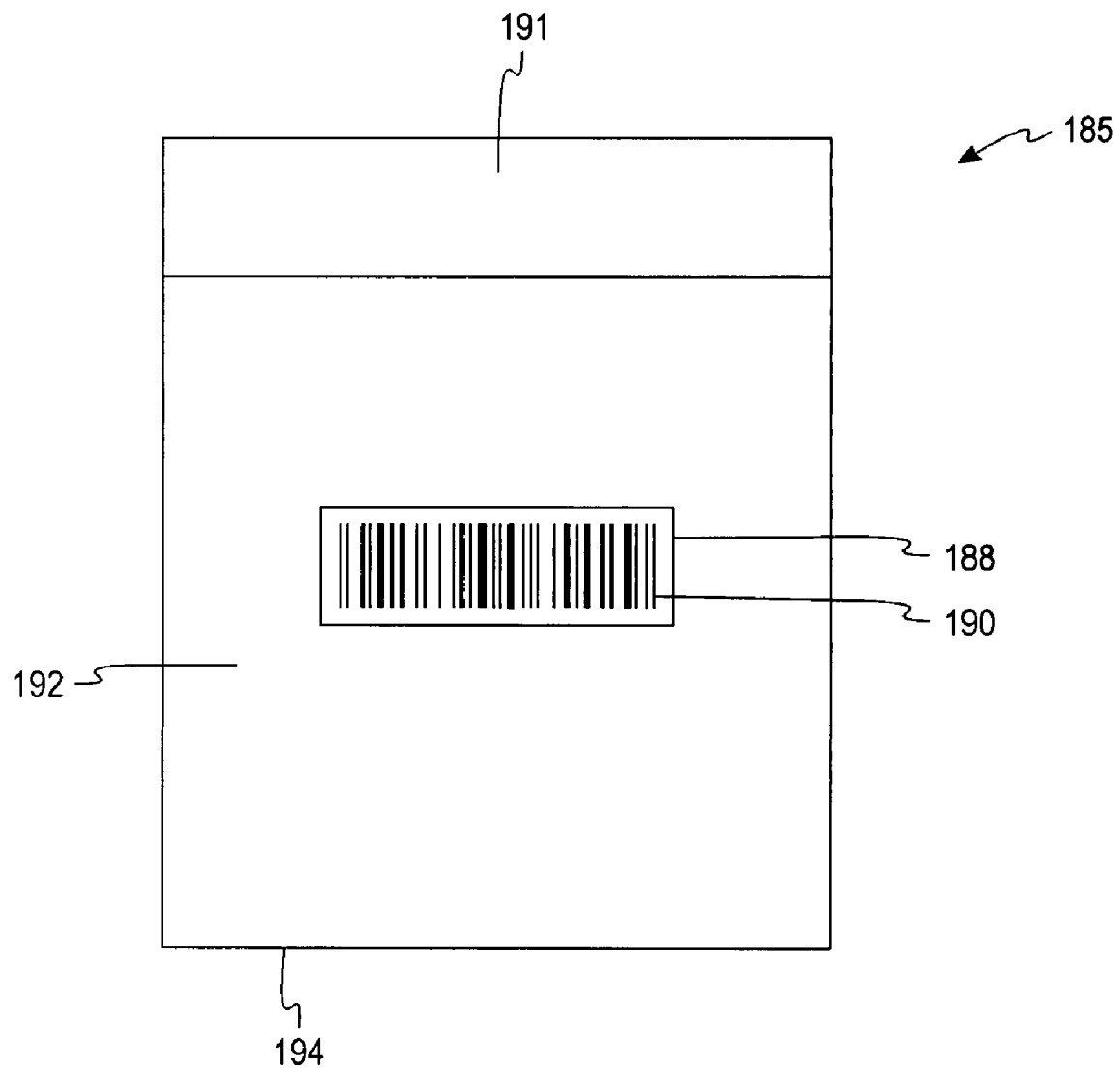
FIG. 3d is a rear view of the cartridge of FIGS. 3a,b.

There are several ways in which mismatching a test-sensor cartridge and a meter and/or testing parameters, programs, and/or protocols of a meter may be inhibited or prevented using the embodiments of the present invention. In one embodiment, for example, the test-sensor cartridge may include a coding feature such as a barcode, an optically detectable feature, or the like adapted to be read by a meter to assist in distinguishing between cartridges, lots, or the like. Referring to FIG. 3d, for example, a test-sensor cartridge 185 includes an autocal label 188 having a barcode 190 thereon. The autocal label 188 is positioned on a portion of the cartridge 185 and/or a lid 191 that is adjacent to a corresponding barcode reader (e.g., barcode reader 191 of FIG. 3c) on a meter (e.g., meter 181 of FIG. 3c) while the cartridge 185 is being unlocked by the meter. Although in the embodiment of FIG. 3d, the autocal label 188 is positioned on a back side 192 of the cartridge 185, it is contemplated that the autocal label 188 may be positioned on other suitable locations including, but not limited to, a bottom 194 of the cartridge 185, the lid 191, combinations thereof, or the like. Upon reading the barcode 190, the meter may adjust its analyte-testing parameters, programs, and/or protocols to correspond with the type and/or generation of test sensors housed within the cartridge 185, thereby increasing the accuracy of the test results.

Alternatively or additionally, the unlocking feature of a meter may be adapted to mate only with a release lock feature of a suitable cartridge(s). Referring back to FIG. 3c, for example, the projection 182 may be positioned, sized, shaped, combinations thereof, or the like to only fit within corresponding apertures (e.g., aperture 166 of FIGS. 3a,b) of compatible cartridges. Thus, a user attempting to unlock a cartridge that is incompatible with the meter 181 using the projection 182 will be unable to do so. The inability to unlock the cartridge will alert the user that the cartridge is incompatible with the meter and, thus, inhibit or prevent inaccurate test results. This embodiment may be used in combination with a coding feature so that the meter may adjust its parameters, programs, and/or protocols to the type and/or generation of test-sensor cartridge being used.

Referring now to FIG. 4a, a cross-sectional view of a test-sensor cartridge 200 and a meter 202 is shown according to another embodiment of the present invention. The cartridge 200 includes at least one aperture 204 and a releasably-locking lid 206. The lid 206 includes a joint 208 coupling a top portion 210 to a side portion 212. The side portion 212 includes at least one tab portion 214. When the cartridge 200 is in the locked position of FIG. 4a, the tab portion 214 extends into the aperture 204 and may not be grasped, pulled, or pushed by a user, thereby making it difficult for the user to open the lid 206.

To open the lid 206, a corresponding unlocking feature or projection 216 positioned on the meter 202 is inserted into the aperture 204 by contacting the cartridge 200 with the meter 202. As shown in FIGS. 4b-c, when the projection 216 contacts the tab portion 214 inside the aperture 204, the tab portion 214 is pushed out from the aperture 204 in the direction of Arrow C, thereby bending the lid 206 at the joint 208. The user may then grasp the side portion 212 and/or the tab portion 214 of the lid 206, open the lid 206, and remove a test sensor from within the cartridge 200.

Figure 5A:
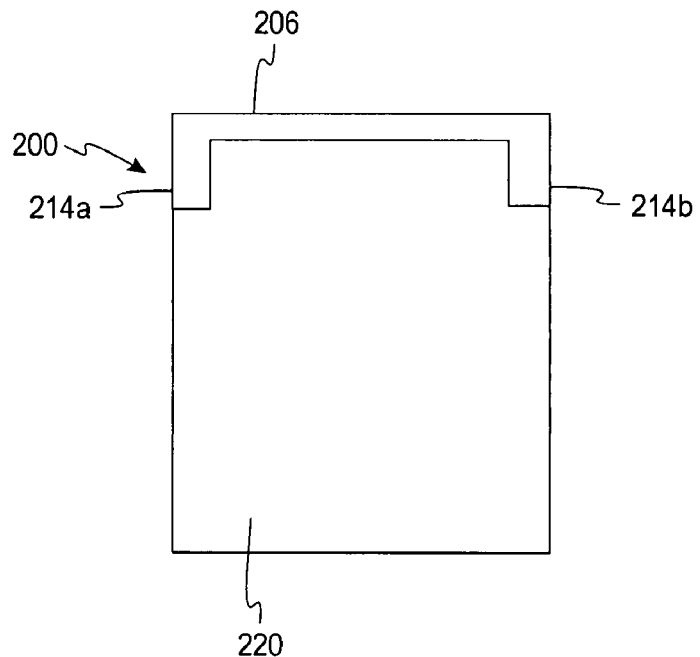
FIG. 5a is a front view of a test-sensor cartridge in a locked position according to one embodiment.
Figure 5B:
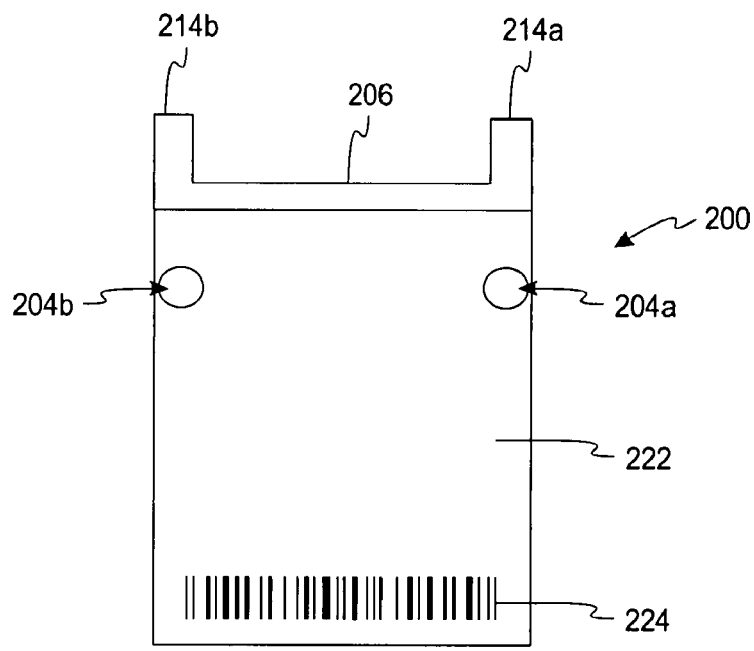
FIG. 5b is a rear view of the test-sensor cartridge of FIG. 5a in an open position.

Any suitable number of apertures 204 and/or projections 216 may be used with the cartridge 200 and the meter 202, respectively. Furthermore, the apertures 204 and/or projections 216 may have any suitable size, shape, position, combinations thereof, or the like. Referring to FIGS. 5a,b, a front side 220 (FIG. 5a) and a back side 222 (FIG. 5b) of the cartridge 200 of FIGS. 4a-c are shown according to one embodiment. FIG. 5a shows the front side 220 of the cartridge 200 in a closed position. FIG. 5b shows the back side 222 of the cartridge 200 in an open position. The cartridge 200 includes two apertures 204a,b that are generally aligned with the tab portions 214 of the lid 206. Thus, according to FIGS. 5a,b, the cartridge 200 is adapted to be used with a meter having two corresponding projections.

According to the embodiment of FIGS. 5a,b, the cartridge 200 includes a barcode 224 on the back side 222 of the cartridge 200. Thus, when the cartridge 200 contacts the meter 202 in order to open the lid 206, a suitably positioned barcode reader 226 (see FIGS. 4a-c) scans and reads the barcode 224. The meter 202 may then recalibrate and/or adjust its testing parameters based on the information obtained from the barcode 224 about the test sensors (not shown) housed within the cartridge 200. As described above with respect to FIGS. 3a-d, in other embodiments, the projection 216 may be positioned, sized, and/or shaped to only fit within apertures of compatible cartridges.

In one embodiment, an autocal label having a barcode thereon is positioned on the underside of the lid 206. In this embodiment, the projection 216 includes a barcode reader thereon. Thus, when the projection 216 is inserted into the aperture 204 to open the lid 206, the barcode reader on the projection 216 reads the barcode on the lid 206. The meter 202 may then recalibrate and/or modify its testing parameters, programs, and/or protocols based on the information about the test sensors in the cartridge 200 gathered from the barcode.

Figure 6:
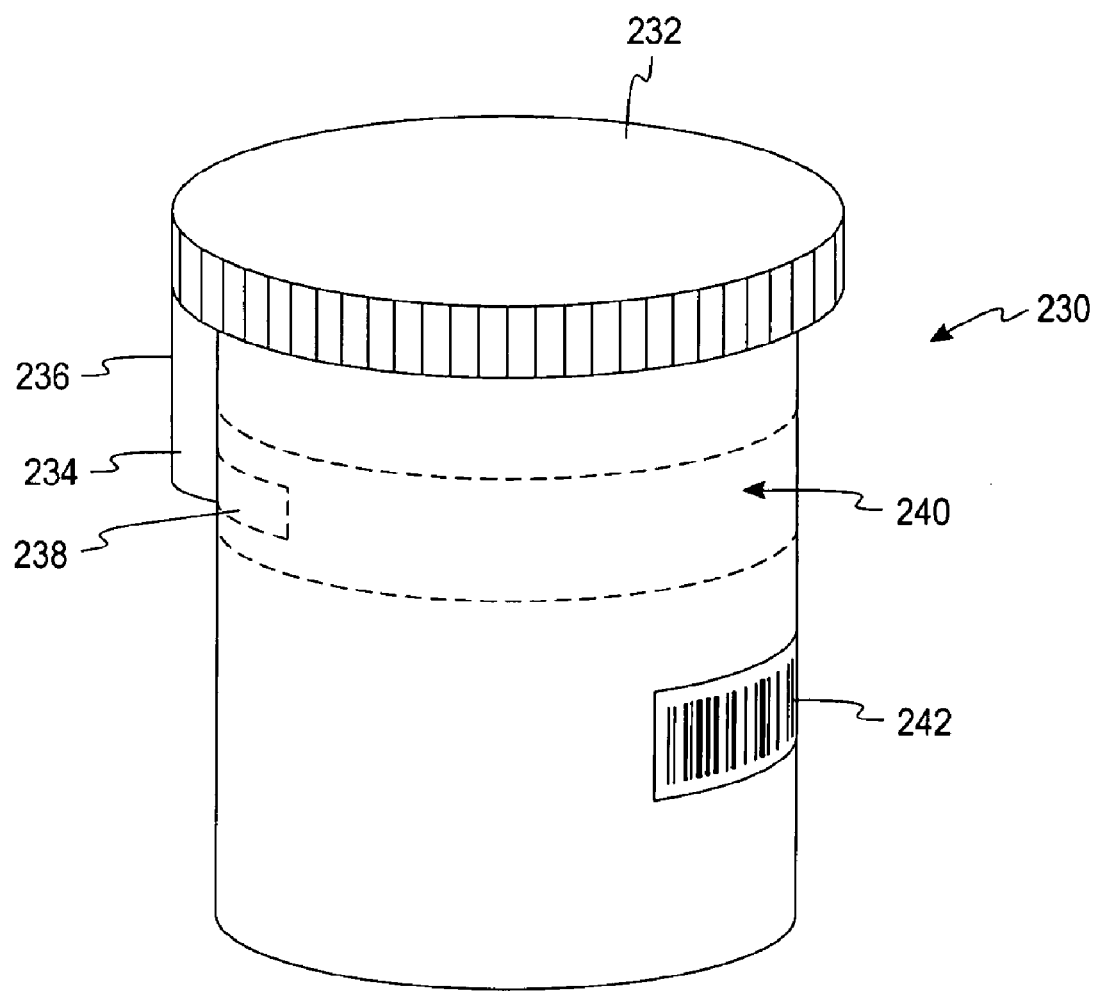
FIG. 6 is a top perspective view of a test-sensor cartridge according to another embodiment of the present invention.

FIG. 6 shows a test-sensor cartridge 230 according to another embodiment of the present invention. Although the cartridge 230 of FIG. 6 is generally round, any suitable shape may be used. The cartridge 230 includes a lid 232 that may be a screw-on type lid, a flick-top type lid, or the like. The lid 232 includes a locking feature 234 having a side portion 236 and a tab portion 238. When the cartridge 230 is in the locked position of FIG. 6, the tab portion extends into an aperture 240 formed within the cartridge 230. The tab portion 238 assists in inhibiting or preventing the lid 232 from being opened by the user without the assistance of a meter. Thus, to open the lid 232 of the cartridge 230, the user must contact the cartridge 230 to a meter (e.g., meter 202 of FIGS. 4a-c) such that a projection (e.g., projection 216 of FIGS. 4a-c) extends through the aperture 240, forcing the tab portion 238 out from the aperture 240. In one embodiment, when the tab portion 238 is forced out from the aperture 240, the locking feature 234 disengages from the lid 232. Thus, the tab portion 238 no longer obstructs movement of the lid 232, and the lid 232 may be freely opened by the user. The lid 232 may be opened manually, or the meter may be further used to facilitate opening.

Any of the ways described above may be used to inhibit or prevent mismatching the cartridge 230 with a meter or parameters, programs, and/or protocols thereof. For example, the cartridge 230 may include a barcode 242 suitably positioned thereon. Alternatively or additionally, the aperture 240 may be sized and/or positioned such that it may only receive projection(s) from a meter(s) with which the cartridge 230 is compatible. Other variations of inhibiting or preventing mismatching the cartridge 230 with a meter may also be used.

Because the cartridges of the embodiments of the present invention must contact a meter to be opened, a user is forced to notify the meter of the type, generation, or the like of the test-sensor cartridge that is being used so that the meter may calibrate and/or modify its testing parameters, programs, and/or protocols accordingly. Such cartridge-to-meter contact must be made before the user can open the cartridge, remove a test sensor, and begin testing. Thus, the chances that the user will forget or choose not to perform the act of notifying the meter that a new cartridge is being used is significantly reduced or eliminated. The embodiments of the present invention may therefore improve the overall accuracy of analyte-testing results.

The embodiments of the present invention also have many other advantages. For example, because the cartridges of the embodiments of the present invention may not be opened without contacting a specific portion of the cartridge to a corresponding specific portion of a meter, the cartridges are generally childproof. Since the test-sensor cartridges of the embodiments of the present invention are coded (e.g., using a barcode, by sizing features of the cartridges to correspond with those of suitable meters, combinations thereof, or the like), the test sensors housed within the cartridges need not be individually coded, which may reduce the costs of manufacturing the sensors.

Alternative Embodiment A

A test-sensor cartridge comprising:
a plurality of test sensors adapted to assist in determining an analyte concentration of a fluid sample;
a plurality of walls forming a cavity therein, the cavity being adapted to include the plurality of test sensors, at least one of the plurality of walls forming at least one aperture;
a lid adapted to enclose the cavity; and
a locking feature adapted to lock the lid to one or more of the walls, the locking feature being adapted to be disengaged by the at least one aperture receiving a projection of an analyte-testing instrument.

Alternative Embodiment B

The cartridge of Alternative Embodiment A, wherein the locking feature includes a latch coupled to the cartridge and a corresponding notch coupled to the lid.

Alternative Embodiment C

The cartridge of Alternative Embodiment A, wherein the locking feature includes a tab portion extending into the aperture.

Alternative Embodiment D

The cartridge of Alternative Embodiment A, wherein the aperture extends completely through the cartridge.

Alternative Embodiment E

The cartridge of Alternative Embodiment A, wherein the cartridge further includes a coding feature positioned such that the coding feature may be read by the analyte-testing instrument when the at least one opening receives the projection.

Alternative Embodiment F

The cartridge of Alternative Embodiment E, wherein the coding feature is located on a surface of the lid adjacent to the cavity and the projection includes a feature for reading the coding feature.

Alternative Embodiment G

The cartridge of Alternative Embodiment A, wherein the aperture is adapted to receive a first projection of a first analyte-testing instrument with which the cartridge is compatible and wherein the aperture may not receive a second projection of a second analyte-testing instrument with which the cartridge is incompatible.

Alternative Embodiment H

A test-sensor cartridge comprising:
a plurality of test sensors adapted to assist in determining an analyte concentration of a fluid sample;
a plurality of walls forming a cavity therein, the cavity being adapted to include the plurality of test sensors, at least one of the walls forming at least one aperture;
a lid adapted to enclose the cavity;
a coding feature positioned on at least one of the walls or the lid; and
a locking feature adapted to lock the lid to one or more of the walls, at least a portion of the locking feature being positioned within the at least one aperture, the locking feature being adapted to be disengaged by the at least one aperture receiving a projection of an analyte-testing instrument, and
wherein the coding feature is adapted to be read by a reading device positioned on the analyte-testing instrument.

Alternative Embodiment I

The cartridge of Alternative Embodiment H, wherein the locking feature includes a latch coupled to the cartridge and a corresponding notch coupled to the lid.

Alternative Embodiment J

The cartridge of Alternative Embodiment H, wherein the locking feature is coupled to the lid, the locking feature further including a tab portion extending into the aperture.

Alternative Embodiment K

The cartridge of Alternative Embodiment H, wherein the aperture extends completely through the cartridge.

Alternative Embodiment L

The cartridge of Alternative Embodiment H, wherein the coding feature is positioned on an exterior surface of one of the walls.

Alternative Embodiment M

The cartridge of Alternative Embodiment H, wherein the coding feature is located on a surface of the lid adjacent to the cavity and the projection includes reading device.

Alternative Embodiment N

The cartridge of Alternative Embodiment H, wherein the aperture is adapted to receive a first projection of a first analyte-testing instrument with which the cartridge is compatible and wherein the aperture may not receive a second projection of a second analyte-testing instrument with which the cartridge is incompatible.

Alternative Process O

A method of modifying testing parameters of an analyte-testing instrument, the method comprising the acts of:
providing a test-sensor cartridge including a plurality of walls forming a cavity therein, the cavity being adapted to include a plurality of test sensors, at least one of the walls forming at least one aperture, the cavity being enclosed by a lid having a locking feature adapted to lock the lid to one or more of the walls, the test sensors being adapted to assist in the determination of a concentration of an analyte in a fluid sample, at least one of the lid or the walls having a coding feature being positioned thereon;
providing an analyte-testing instrument having at least one projection located thereon, the analyte-testing instrument including a reading device;
disengaging the locking feature by contacting the cartridge to the analyte-testing instrument such that the at least one projection mates with the at least one aperture;
reading the coding feature using the reading device;
modifying at least one testing parameter of the analyte-testing instrument based on information received by reading the coding feature.

Alternative Process P

The method of Alternative Process O, wherein the locking feature includes a latch coupled to the cartridge and a corresponding notch coupled to the lid.

Alternative Process Q

The method of Alternative Process O, wherein the locking feature includes a tab portion extending into the aperture.

Alternative Process R

The method of Alternative Process O, wherein the aperture extends completely through the cartridge.

Alternative Process S

The method of Alternative Process O, wherein the coding feature is located on a surface of the lid adjacent to the cavity and the reading device is positioned on the at least one projection.

Alternative Process T

The method of Alternative Process O, wherein the act of disengaging the locking feature includes the at least one projection forcing the locking feature out from the at least one aperture.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. An analyte-testing system for determining an amount of an analyte in a fluid test sample, the analyte-testing system comprising:
a test-sensor cartridge including
a plurality of test sensors,
a plurality of walls forming a cavity therein, the cavity being adapted to include the plurality of test sensors, at least one of the walls forming at least one aperture,
a lid adapted to enclose the cavity, and
a locking feature adapted to lock the lid to one or more of the walls, at least a portion of the locking feature being positioned within the at least one aperture; and
an analyte-testing instrument including
a body portion,
at least one opening formed in the body portion, the at least one opening being configured to receive one of the plurality of test sensors, and
at least one projection extending from the body portion, the locking feature being adapted to be disengaged by the at least one aperture receiving the at least one projection of the analyte-testing instrument.

2. The analyte-testing system of claim 1, wherein the locking feature includes a latch coupled to the cartridge and a corresponding notch coupled to the lid.

3. The analyte-testing system of claim 1, wherein the locking feature is coupled to the lid, the locking feature further including a tab portion extending into the aperture.

4. The analyte-testing system of claim 1, wherein the aperture extends completely through the cartridge.

5. The analyte-testing system of claim 1, wherein the coding feature is positioned on an exterior surface of one of the walls.

6. The analyte-testing system of claim 1, the test-sensor cartridge further including a coding feature positioned on at least one of the walls or the lid, the coding feature being adapted to be read by a reading device positioned on the analyte-testing instrument.

7. The analyte-testing system of claim 6, wherein the coding feature is located on a surface of the lid adjacent to the cavity and the projection includes reading device.

8. The analyte-testing system of claim 6, wherein the aperture is adapted to receive a first projection of a first analyte-testing instrument with which the cartridge is compatible and wherein the aperture may not receive a second projection of a second analyte-testing instrument with which the cartridge is incompatible.

9. A method of modifying testing parameters of an analyte-testing instrument, the method comprising the acts of:
providing a test-sensor cartridge including a plurality of walls forming a cavity therein, the cavity being adapted to include a plurality of test sensors, at least one of the walls forming at least one aperture, the cavity being enclosed by a lid having a locking feature adapted to lock the lid to one or more of the walls, the test sensors being adapted to assist in the determination of a concentration of an analyte in a fluid sample, at least one of the lid or the walls having a coding feature being positioned thereon;
providing an analyte-testing instrument having at least one projection located thereon, the analyte-testing instrument including a reading device;
disengaging the locking feature by contacting the cartridge to the analyte-testing instrument such that the at least one projection mates with the at least one aperture;
reading the coding feature using the reading device;
modifying at least one testing parameter of the analyte-testing instrument based on information received by reading the coding feature.

10. The method of claim 9, wherein the locking feature includes a latch coupled to the cartridge and a corresponding notch coupled to the lid.

11. The method of claim 9, wherein the locking feature includes a tab portion extending into the aperture.

12. The method of claim 9, wherein the aperture extends completely through the cartridge.

13. The method of claim 9, wherein the coding feature is located on a surface of the lid adjacent to the cavity and the reading device is positioned on the at least one projection.

14. The method of claim 9, wherein the act of disengaging the locking feature includes the at least one projection forcing the locking feature out from the at least one aperture.

* * * * *